United States Patent
Feins et al.

(10) Patent No.: US 11,433,161 B2
(45) Date of Patent: Sep. 6, 2022

(54) AUTONOMOUSLY GROWING IMPLANTABLE DEVICE

(71) Applicants: Children's Medical Center Corporation, Boston, MA (US); The Brigham and Women's Hospital, Inc., Boston, MA (US)

(72) Inventors: Eric N. Feins, Boston, MA (US); Pedro J. del Nido, Lexington, MA (US); Nikolay V. Vasilyev, Brookline, MA (US); Haruo Yamauchi, Tokyo (JP); Douglas P. Perrin, Boston, MA (US); Peter E. Hammer, Needham, MA (US); Veaceslav Arabagi, Cambridge, MA (US); Jeffrey M. Karp, Brookline, MA (US); Yuhan Lee, Cambridge, MA (US); Eoin D. O'Cearbhaill, Cambridge, MA (US)

(73) Assignees: Children's Medical Center Corporation, Boston, MA (US); The Brigham and Women's Hospital, Inc., Boston, MA (US)

(*) Notice: Subject to any disclaimer, the term of this patent is extended or adjusted under 35 U.S.C. 154(b) by 0 days.

(21) Appl. No.: 17/146,464

(22) Filed: Jan. 11, 2021

(65) Prior Publication Data

US 2021/0205492 A1    Jul. 8, 2021

Related U.S. Application Data

(62) Division of application No. 16/077,787, filed as application No. PCT/US2017/018187 on Feb. 16, 2017, now Pat. No. 10,905,795.

(Continued)

(51) Int. Cl.
*A61L 27/16* (2006.01)
*A61B 17/70* (2006.01)
(Continued)

(52) U.S. Cl.
CPC .......... *A61L 27/16* (2013.01); *A61B 17/7002* (2013.01); *A61F 2/2445* (2013.01);
(Continued)

(58) Field of Classification Search
CPC ...... A61L 27/16; A61B 17/7002; C08G 18/10
See application file for complete search history.

(56) References Cited

U.S. PATENT DOCUMENTS

| 4,042,979 A | 8/1977 | Angell |
| 5,061,277 A | 10/1991 | Carpentier et al. |

(Continued)

FOREIGN PATENT DOCUMENTS

| EP | 0 338 994 A1 | 10/1989 |
| WO | WO 95/31948 A1 | 11/1995 |

(Continued)

OTHER PUBLICATIONS

PCT/US2017/018187, May 30, 2017, International Search Report and Written Opinion.

(Continued)

*Primary Examiner* — Jason-Dennis N Stewart
(74) *Attorney, Agent, or Firm* — Wolf, Greenfield & Sacks, P.C.

(57) ABSTRACT

An implantable, autonomously growing medical device is disclosed. The device may have an outer, braided outer element that holds an inner core. Degradation and/or softening of the inner core permits the outer element to elongate, allowing the device to grow with surrounding tissue. The growth profile of the medical device can be controlled by (Continued)

altering the shape/material/cure conditions of the inner core, as well as the geometry of the out element.

4 Claims, 16 Drawing Sheets

Related U.S. Application Data

(60) Provisional application No. 62/295,768, filed on Feb. 16, 2016.

(51) Int. Cl.
| | |
|---|---|
| A61F 2/24 | (2006.01) |
| A61F 2/28 | (2006.01) |
| A61L 27/18 | (2006.01) |
| A61L 27/58 | (2006.01) |
| B29C 67/24 | (2006.01) |
| C08G 63/16 | (2006.01) |
| C08G 63/91 | (2006.01) |
| A61B 17/00 | (2006.01) |
| A61F 2/30 | (2006.01) |

(52) U.S. Cl.
CPC ............... *A61F 2/28* (2013.01); *A61L 27/18* (2013.01); *A61L 27/58* (2013.01); *B29C 67/24* (2013.01); *C08G 63/16* (2013.01); *C08G 63/916* (2013.01); *A61B 2017/00862* (2013.01); *A61F 2002/2892* (2013.01); *A61F 2002/30062* (2013.01); *A61F 2002/30069* (2013.01); *A61F 2002/30224* (2013.01); *A61F 2002/30706* (2013.01); *A61F 2230/0069* (2013.01); *A61F 2250/0082* (2013.01); *B29K 2995/006* (2013.01)

(56) References Cited

U.S. PATENT DOCUMENTS

| | | |
|---|---|---|
| 5,593,435 A | 1/1997 | Carpentier et al. |
| 5,888,240 A | 3/1999 | Carpentier et al. |
| 6,159,240 A | 12/2000 | Sparer et al. |
| 6,217,610 B1 | 4/2001 | Carpentier et al. |
| 6,391,054 B2 | 5/2002 | Carpentier et al. |
| 7,163,562 B2 | 1/2007 | Datta et al. |
| 7,722,668 B2 | 5/2010 | Moaddeb et al. |
| 8,105,376 B2 | 1/2012 | Ryan et al. |
| 8,764,813 B2 | 7/2014 | Jantzen et al. |
| 10,905,795 B2 | 2/2021 | Feins et al. |
| 2007/0055368 A1 | 3/2007 | Rhee et al. |
| 2007/0078480 A1 | 4/2007 | Belenkaya et al. |
| 2012/0209379 A1 | 8/2012 | Shaolian et al. |
| 2013/0236498 A1 | 9/2013 | Mangiardi |
| 2020/0054785 A1 | 2/2020 | Feins et al. |

FOREIGN PATENT DOCUMENTS

| | | |
|---|---|---|
| WO | WO 03/064496 A2 | 8/2003 |
| WO | WO 2005/063317 A1 | 7/2005 |

OTHER PUBLICATIONS

PCT/US2017/018187, Aug. 21, 2018, International Preliminary Report on Patentability.
EP 17753844.4, Oct. 1, 2019, Extended European Search Report.
International Search Report and Written Opinion dated May 30, 2017 in connection with International Application No. PCT/US2017/018187.
International Preliminary Report on Patentability dated Aug. 21, 2018 in connection with International Application No. PCT/US2017/018187.
Extended European Search Report dated Oct. 1, 2019 in connection with European Application No. 17753844.4.
Lopes et al., Acrylic formulations containing bioactive and biodegradable fillers to be used as bone cements: Properties and biocompatibility assessment. Materials Science and Engineering C. Dec. 13, 2013;33(3):1289-1299.
Yarin, Coaxial electrospinning and emulsion electrospinning of core-shell fibers. Polymers for Advanced Technologies. Jan. 1, 2011: 22(3):310-317.

FIG. 1A
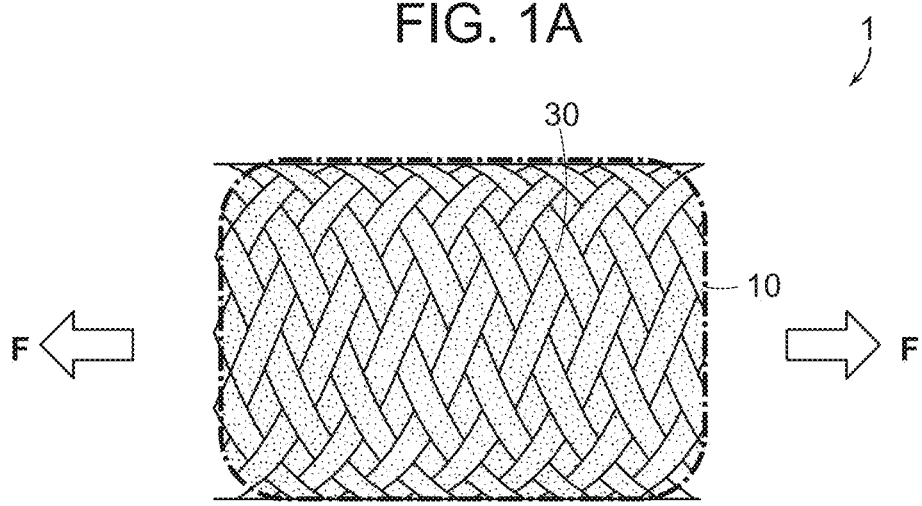
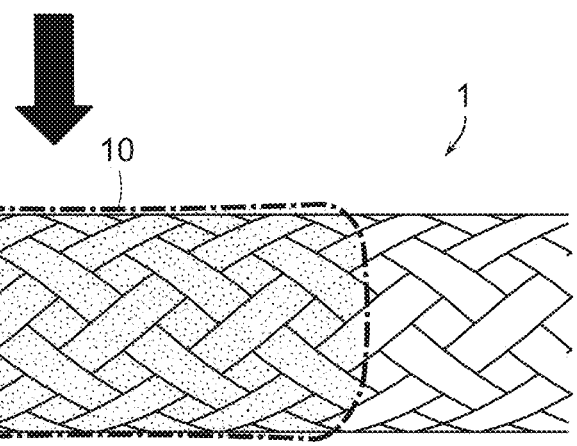
FIG. 1B

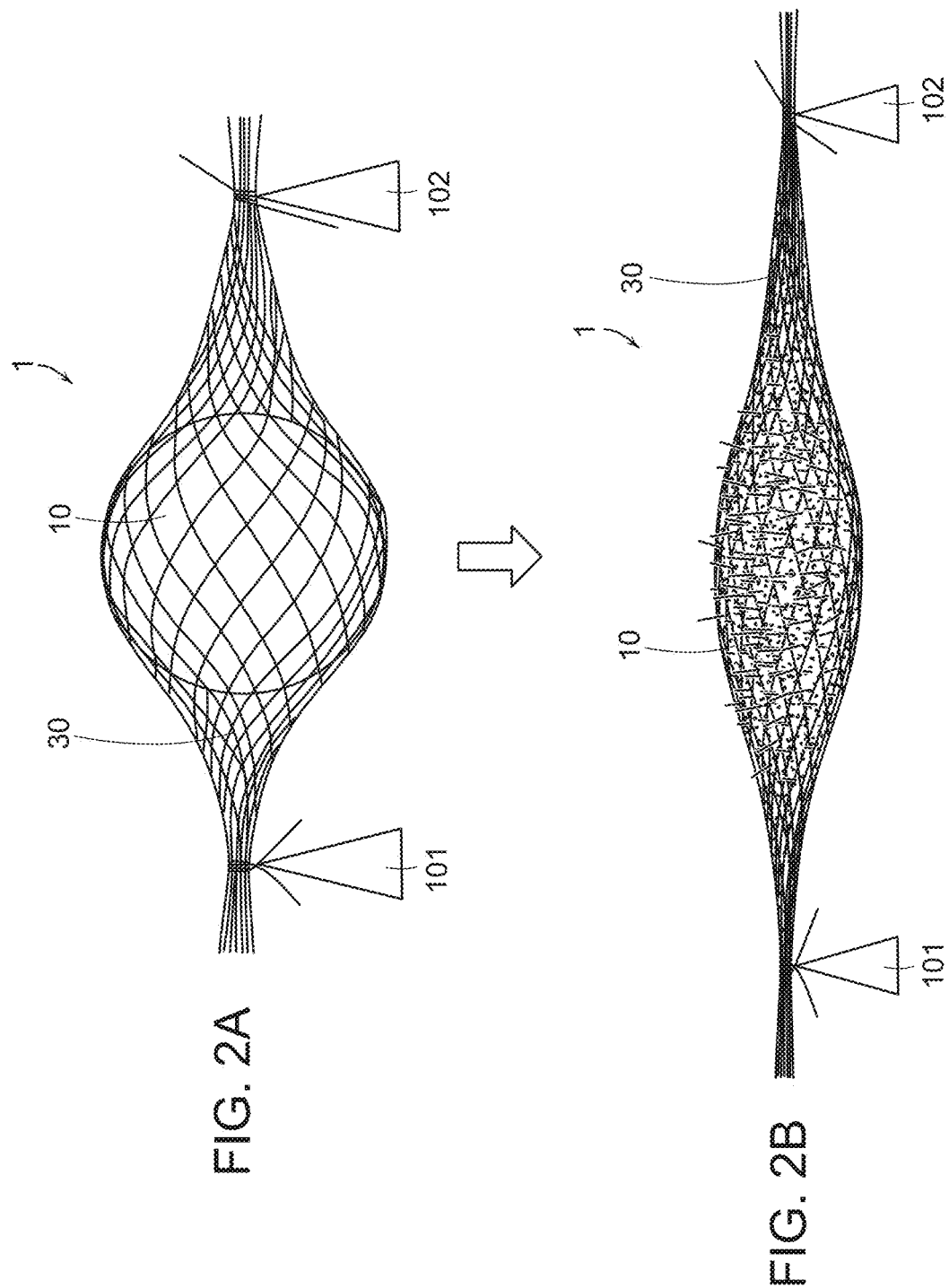

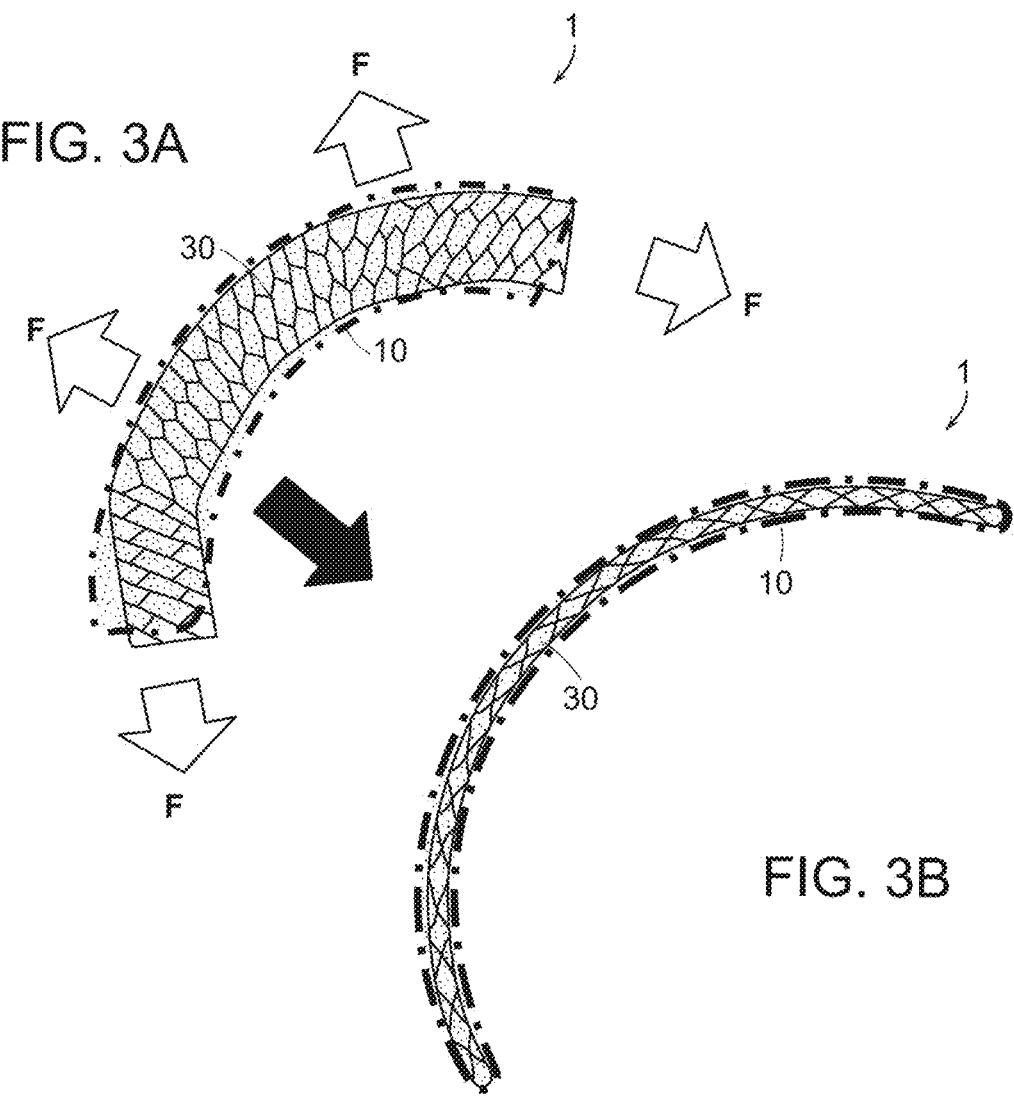

FIG. 4A
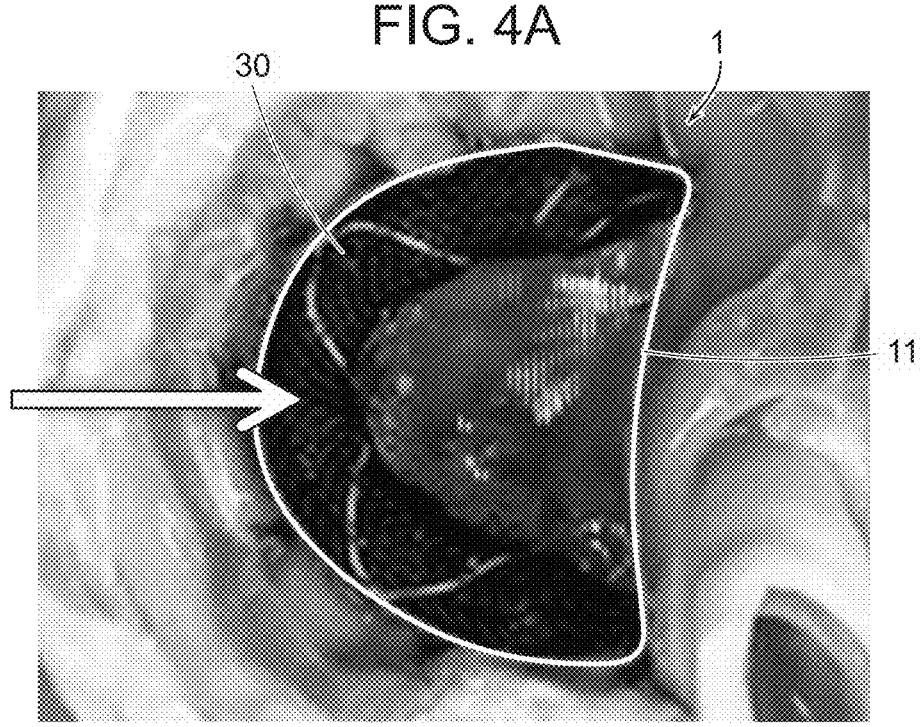
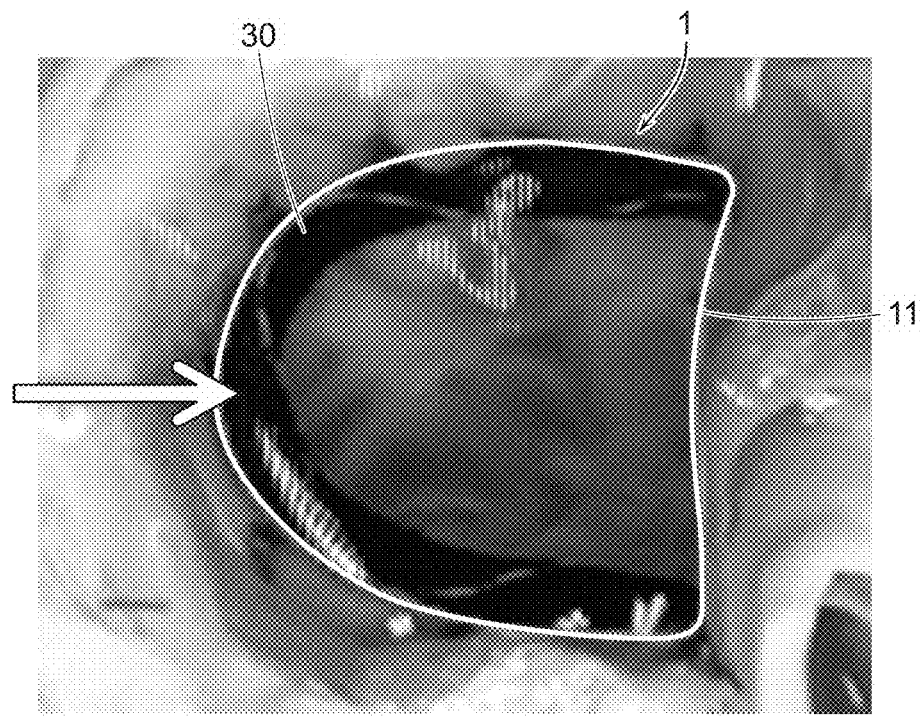
FIG. 4B

AUTONOMOUSLY GROWING IMPLANTABLE DEVICE

RELATED APPLICATIONS

This application is a divisional of application Ser. No. 16/077,787, entitled "AUTONOMOUSLY GROWING IMPLANTABLE DEVICE," filed on Aug. 14, 2018, which is a national stage filing under 35 U.S.C. 371 of International Patent Application Serial No. PCT/US2017/018187, entitled "AUTONOMOUSLY GROWING IMPLANTABLE DEVICE" filed on Feb. 16, 2017, which claims the benefit under 35 U.S.C. § 119(e) of U.S. Provisional Application Ser. No. 62/295,768, entitled "AUTONOMOUSLY GROWING IMPLANTABLE DEVICE" filed on Feb. 16, 2016, the entire contents of each of which are incorporated herein by reference.

BACKGROUND

1. Field

Aspects described herein relate generally to an autonomously growing implantable device.

2. Discussion of Related Art

Conventional medical devices used to treat anatomic and morphologic defects are fixed in size. Biodegradable annuloplasty rings that have been developed for use in children provide temporary annular support until they completely degrade.

SUMMARY

In an illustrative embodiment, an implantable device is provided. The implantable device includes an outer element having a first length. The device also includes an inner core disposed within the outer element. Presence of the inner core limits elongation of the outer element. Degradation of the inner core permits elongation of the outer element from the first length to a second length that is longer than the first length.

In another illustrative embodiment, a method of using an implantable device is provided. The method includes providing an outer element with an inner core disposed within the outer element. The method also includes coupling the outer element to an implantation site. Contacting the inner core with body fluid at the implantation site initiates degradation of the inner core. Degradation of the inner core permits elongation of the outer element from a first length to a second length that is longer than the first length. The length of the outer element changes from the first length to the second length in response to degradation of the inner core and to forces from native growing tissue at the implantation site acting on the outer element.

In yet another illustrative embodiment, a method of forming a biodegradable polymer is provided. The method includes polycondensation of an equimolar ratio of glycerol and sebacic acid at 120° C. for 8 hours under dry nitrogen and for 16 hours in vacuum to form a pre-polymer. The method also includes curing the pre-polymer in a vacuum at a temperature of 140° C. to 160° C. for 40 to 100 hours.

In yet another illustrative embodiment, a polymer is provided. The polymer has a Young's Modulus of greater than 5 MPa and a crosslinking density of 600 to 12,000 mols per cubic meter. The polymer is formed from curing a poly(glycerol sebacate) pre-polymer in vacuum at a temperature of 140° C. to 160° C. for 40 to 100 hours.

Various embodiments provide certain advantages. Not all embodiments of the present disclosure share the same advantages and those that do may not share them under all circumstances.

Further features and advantages of the present disclosure, as well as the structure of various embodiments are described in detail below with reference to the accompanying drawings.

BRIEF DESCRIPTION OF THE DRAWINGS

Various embodiments will now be described, by way of example, with reference to the accompanying drawings, in which:

FIG. 1A depicts a schematic representation of an embodiment of an implantable device in accordance with one aspect;

FIG. 1B depicts a schematic representation of the implantable device of FIG. 1A exhibiting growth in one dimension;

FIG. 2A depicts an embodiment of an implantable device in accordance with one aspect;

FIG. 2B depicts the implantable device of FIG. 2A exhibiting growth in one dimension;

FIG. 3A depicts a schematic representation of another embodiment of an implantable device in accordance with one aspect;

FIG. 3B depicts a schematic representation of the implantable device of FIG. 3A exhibiting growth in two dimensions;

FIG. 4A depicts an embodiment of an implantable device used in a heart valve annuloplasty application in accordance with one aspect;

FIG. 4B depicts a schematic representation of the implantable device of FIG. 4A exhibiting growth in two dimensions;

DETAILED DESCRIPTION

Figure 5:
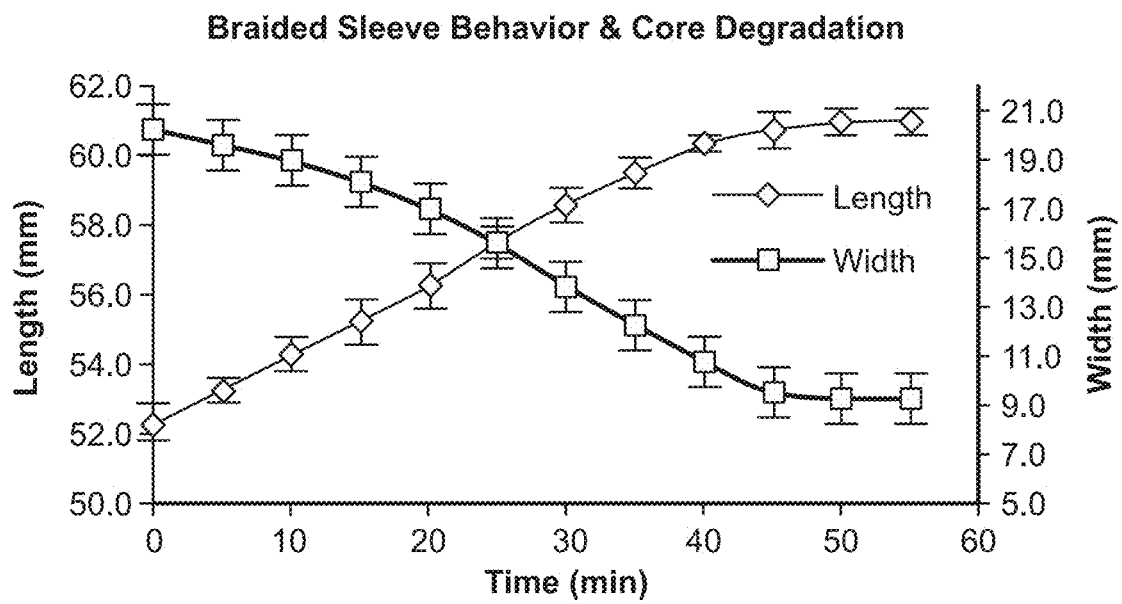
FIG. 5 depicts a graph showing the relationship between outer element behavior and inner core degradation.

Over 400,000 surgeries are performed annually on children in the United States to correct anatomic and morphologic defects. Medical implants that can respond to and guide tissue growth represent a longstanding unmet clinical need, especially for use in the treatment of pediatric surgical conditions. The inventors have recognized that existing device implants that have a fixed size have limited application in growing children. Use of fixed-size implants in children leads to growth restriction and requires eventual device removal, subjecting children to repeated surgical procedures and increased complication rates.

In some cases, such as pediatric heart valve surgery, fixed-size implants are avoided due to the deleterious effects of growth restriction on the heart. While prosthetic implants have greatly improved the durability of surgical repair in adults, the lack of growing implants for children has led to poorer outcomes. Currently available prosthetic rings, which are implanted on the annulus of dilated heart valves, may not, in some circumstances, be suitable for use in children, because the fixed size of the rings may restrict normal valve growth and may cause stenosis over time. Another available device is a biodegradable annuloplasty ring, which provides temporary annular support until it completely degrades. Given that the biodegradable ring inevitably loses mechanical integrity, such a device may be subject to mechanical failure.

As a result, pediatric heart surgeons often rely on suture-based annuloplasty techniques. In such techniques, the repair sutures break or pull through the tissue over time allowing for valve growth. However, this stretching and loss of tissue anchoring is unpredictable and predisposes patients to pathologic re-dilation of the valve and recurrence of valve dysfunction. The lack of a suitable prosthetic device that can grow with a growing patient to provide ongoing annular support is one reason pediatric heart repair outcomes lag behind those of adults. Over 80% of adult tricuspid valve repairs using a prosthetic ring do not have recurrent valve dysfunction or re-operation 15 years after surgery. In contrast, successful valve repair is achieved in only 50% of children with single-ventricle anatomy, and failed repair is an independent risk factor for mortality.

Pediatric orthopedic disorders involving abnormal long-bone growth (e.g. limb-length discrepancy and angular limb deformities) were historically treated with invasive surgical osteotomies to provide immediate skeletal correction. These surgeries carried significant morbidity, including post-operative pain, requisite activity restriction, and nerve and vascular injury. Recently, techniques using internal fixators (e.g. staples and plated systems) implanted across the growth plate have been adopted, which are less morbid and enable more gradual repair of skeletal deformities. Unfortunately, the existing fixed-size implants must be removed after deformity correction to prevent excessive growth restriction, thus subjecting children to additional surgical procedures. Moreover, after device removal, children are at risk for rebound growth, recurrent limb deformation, and need for repeated surgical interventions.

Surgical correction of scoliosis has similar limitations. Traditional surgical repair techniques involved spinal fusion procedures, which impeded spinal growth and led to pulmonary insufficiency in children. More recently, "growing" rod systems have been developed and are a common surgical repair technique. While the growing rod system permits ongoing spinal and thoracic growth, the implantable device does not autonomously grow. Frequent interventions are required to lengthen the rods, with some children requiring as many as fifteen surgical procedures. Complication rates approach 60%, and each surgery increases the likelihood of a child experiencing a complication by 24%.

Accordingly, the inventors have recognized a need for medical devices that can grow autonomously to enable more durable surgical repairs and to eliminate the need for repeated surgical interventions in growing patients, particularly in children.

Described herein is an autonomously growing implantable device for supporting tissue to correct anatomic and morphologic defects. The device can, in some embodiments, be used for pediatric applications.

The device comprises a unique form of an inner core located inside an outer element that surrounds the inner core. The outer element is configured such that a decrease in width or diameter of the outer element results in an increase in length of the outer element, and vice versa. Described another way, in some embodiments, the outer element is configured such that an increase in one dimension of the outer element results in a decrease in a second dimension of the outer element and vice versa, the second dimension being perpendicular to the first dimension.

In some embodiments, the outer element is shaped in a tubular sleeve. However, it should be appreciated that other arrangements of the outer element are possible, such as a sleeve with a rectangular, square, triangular or other cross section, a spherical or ellipsoidal shape, or other suitable shape that surrounds the inner core, where change in diameter or width of the outer element results in change in length of the outer element, and vice versa.

The presence of the inner core inside the outer element limits the length of the outer element by preventing the outer element from elongating. As the inner core gradually degrades and/or softens following surgical implantation of the device, the outer element is permitted to gradually elongate to accommodate native tissue growth. The device is designed to initially restrict growth/expansion of the native tissue to which the device is coupled, but as the inner core degrades and/or softens over time, the device may grow at a pre-determined rate to guide tissue growth. The growth profile of the device may be customizable by adjusting one or more features of the device.

In some embodiments, an implantable device is configured to undergo growth in one dimension (i.e., elongation). FIGS. 1A-1B depict schematic representations of an embodiment of an implantable device exhibiting growth in one dimension. Implantable device 1 includes an outer element 30 and an inner core 10 (the inner core is outlined in dot-dash-dot lines). In some embodiments, such as the one shown in FIGS. 1A-1B, the outer element takes the shape of a tubular sleeve. In the first stage, shown in FIG. 1A, the presence of the inner core 10 sets the diameter of the sleeve 30, and prohibits the sleeve 30 from lengthening, even when subject to external forces F.

The outer element is coupled to the native growing tissue located at the implantation site (e.g. bone, cardiac tissue, etc.). As the tissue at the implantation site grows (e.g. bone lengthening, heart valve annulus expanding, etc.), the growing tissue, which is coupled to the outer element of the implantable device, generates a force F that acts on the outer element.

As the inner core 10 degrades and/or softens, the diameter of the outer element 30 is permitted to decrease. Due to the external forces F applied on the outer element 30 by the growing native tissue, the diameter of the outer element 30 decreases and the outer element elongates, resulting in the second stage, in which the device has grown in length, shown in FIG. 1B.

FIGS. 2A-2B depict an embodiment of an implantable device used for applications in which growth in only one dimension is desirable, such as long-bone orthopedic applications. Gradual degradation and/or softening of the inner core 10 permits gradual decrease in the diameter of the outer element 30, and concomitant device elongation in one dimension in response to applied external forces pulling on the ends of the outer element. As seen when comparing FIG. 2A to FIG. 2B, the distance between the first end 101 of the implantable device 1 and the second end 102 of the implantable device increases as the inner core 10 degrades and/or softens.

In some embodiments, an implantable device is configured to undergo growth in two dimensions while the diameter of the device decreases. Described another way, with devices that are not straight, as the overall length of the device increases, the device expands in two dimensions while the diameter of the device decreases. In the case of a ring-shaped or curved/bent band device, growing in two dimensions means that the area circumscribed by the ring-shaped or curved/bent band device increases.

FIGS. 3A-3B depict schematic representations of an embodiment of an implantable device exhibiting growth in two dimensions. Implantable device 1 includes a curved outer element 30 and an inner core 10. In the first stage, shown in FIG. 3A, the presence of the inner core 10 sets the diameter of the outer element 30, and prohibits the outer element 30 from elongating, even when subject to the external forces F generated from native growing tissue at the site of implantation. As the inner core 10 degrades and/or softens, the diameter of the outer element 30 is permitted to decrease. As the diameter of the outer element 30 decreases, the outer element elongates in reaction to external forces F, resulting in the second stage, where the device has grown in two dimensions, shown in FIG. 3B.

Implantable devices that are configured to undergo growth in two dimensions can serve as autonomously growing heart valve annuloplasty devices such as rings or curved/bent bands. FIGS. 4A-4B depict an embodiment of an implantable device used for heart valve annuloplasty applications. The device is configured to grow in two dimensions. Gradual degradation and/or softening of the inner core 10 leads to gradual decrease in the diameter of the outer element 30 and concomitant growth in two dimensions. As seen when comparing FIG. 4A to 4B, the length of the implantable device increases as the inner core 10 degrades and/or softens. Said another way, the device, which is in the form of an annuloplasty device, expands in two dimensions as the inner core 10 degrades and/or softens. In FIGS. 4A and 4B, the drawn outline 11 is not part of the implantable device; it is an outline of the area circumscribed by the annuloplasty band device, and also represents the outline of the valve orifice. This outline 11 shows that expansion of the annuloplasty band permits expansion of the valve orifice.

As discussed above, the implantable device is configured such that degradation of the inner core leads to gradual decrease in the inner core diameter/size, which allows the outer element to increase in length. One example of the relationship between the outer element behavior and inner core degradation is shown in the graph depicted in FIG. 5. The graph illustrates that inner core degradation permits braided outer element elongation and gradual ring/band expansion. It should be noted that the graph depicted in FIG. 5, along with FIGS. 6 and 7, reflect the results of accelerated degradation studies. It is contemplated that actual implantable devices to be used in human patients would degrade and/or soften over longer periods of time, e.g., months or years.

Figure 6:
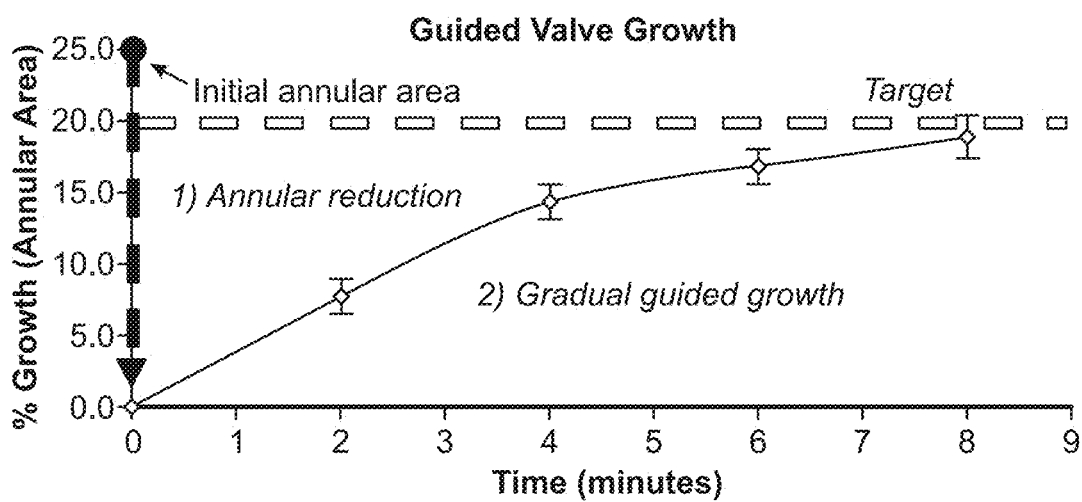
FIG. 6 depicts data from an ex vivo demonstration of controlled valve growth using an autonomously growing implantable device.

The implantable device described herein can be used to initially restrict tissue growth, and then gradually support and guide tissue growth along a predetermined profile. FIG. 6 depicts data from an ex vivo demonstration of controlled valve growth using an autonomously growing implantable device with degradable cores. The initial valve area was 877.2±141.2 mm$^2$. With device implantation, the valve area reduced to 650.6±55.3 mm$^2$ (25% reduction). Due to degradation of the core, the device could elongate, leading to controlled heart valve area growth to the target valve area of 780 mm$^2$ (20% growth). This study demonstrates that an implantable device can be used to initially reduce the size of the native tissue at the implantation site and/or restrict growth of native tissue, and then gradually guide the growth of the tissue over time as the inner core of the device degrades and/or softens.

The Inner Core

The inner core can be made from a material that changes in reaction to contact with body fluids. The inner core may be biodegradable, and/or it may be a material that becomes softer over time when placed in contact with body fluids.

In some embodiments, the inner core is made of a polymer, such as a modified polymer poly(glycerol sebacate) (PGS), hereinafter referred to as "extra-strong PGS" or "ESPGS." In some embodiments, ESPGS can be synthesized using reaction conditions that achieve increased cross-linking between polymers. In some cases, synthesis of ESPGS occurs in vacuum within polytetrafluoroethylene (PTFE) cylindrical molds. Different curing conditions for ESPGS are possible, and changes in curing conditions give rise to differences in various properties such as degradation rates and the Young's modulus of the polymer. As such, certain curing conditions can be chosen to achieve a desired degradation rate and/or a desired Young's modulus.

In one example, to make ESPGS, a viscous PGS pre-polymer was synthesized via catalyst-free, solvent-free polycondensation of 0.1 mol each of glycerol and sebacic acid (or other equimolar ratio) at 120° C. for 8 hours in a nitrogen environment (e.g., under dry nitrogen) and for 16 hours in vacuum. The resultant viscous pre-polymer was then injected into thin-walled PTFE tubing (inner diameter=1.8 mm), which acted as a sacrificial mold. The PGS pre-polymer may then be cured in vacuum (e.g., in a vacuum oven) at 140° C. to 160° C. for 40 to 100 hours. In one embodiment, after being injected into the PTFE tubing, the PGS pre-polymer is cured in a vacuum oven at 155° C. for 86 hours, resulting in 1.8 mm ESPGS cylinders.

In some embodiments, prior to degradation, ESPGS limits stretching of a device to less than 5%.

The PGS pre-polymer may be cured at different temperatures to form ESPGS. In some embodiments, the PGS pre-polymer is cured at a temperature of 120-140° C., 125-135° C., 128-132° C. or 130° C. In other embodiments, the PGS pre-polymer is cured at a temperature of 145-165° C., 150-160° C., 153-157° C. or 155° C.

The PGS pre-polymer may also be cured for different lengths of time to form ESPGS. In some embodiments, the PGS pre-polymer is cured for 40-100 hours, 70-100 hours, 80-90 hours, 84-88 hours, at 86 hours. In other embodiments, the PGS pre-polymer is cured for 30-65 hours, 45-55 hours, 46-50 hours, or at 48 hours.

For example, in some embodiments, the PGS pre-polymer is cured at 155° C. for 86 hours or for 48 hours. In some embodiments, the PGS pre-polymer is cured at 130° C. for 86 hours or for 48 hours. In some embodiments, the PGS pre-polymer is cured at a temperature of over 150° C. for over 80 hours.

In some embodiments, the curing duration and temperature can be varied based on clinical application to achieve device elongation profiles that span from months to years.

Figure 7:
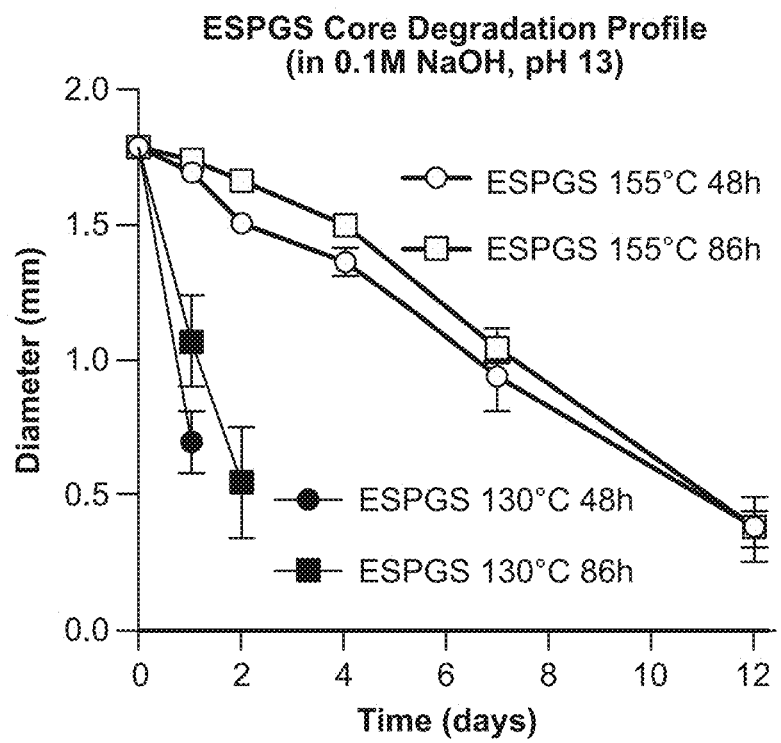
FIG. 7 depicts a graph showing different polymer degradation rates resulting from different curing conditions.

FIG. 7 depicts a graph showing different ESPGS degradation rates for different polymer curing conditions in accelerated degradation studies using a strong base (0.1 M NaOH solution in water, pH 13.0). FIG. 7 shows that using a higher cure temperature of 155° C. leads to slower degradation rates as compared to a lower cure temperature of 130° C. As such, in some cases, if slower degradation rate is desired, a higher cure temperature may be a suitable choice, and if a faster degradation rate is desired, a lower cure temperature may be a suitable choice. As shown in FIG. 7, the degradation rate of ESPGS was 9.2-fold slower than that of conventional PGS, suggesting that complete degradation of ESPGS in physiological conditions could be adjusted depending upon the clinical application. In some embodiments, when kept in a NaOH solution in water having a pH of 13.0, the ESPGS degradation rate ranges from 0.05 to 1.0 mm/week.

Figure 8:
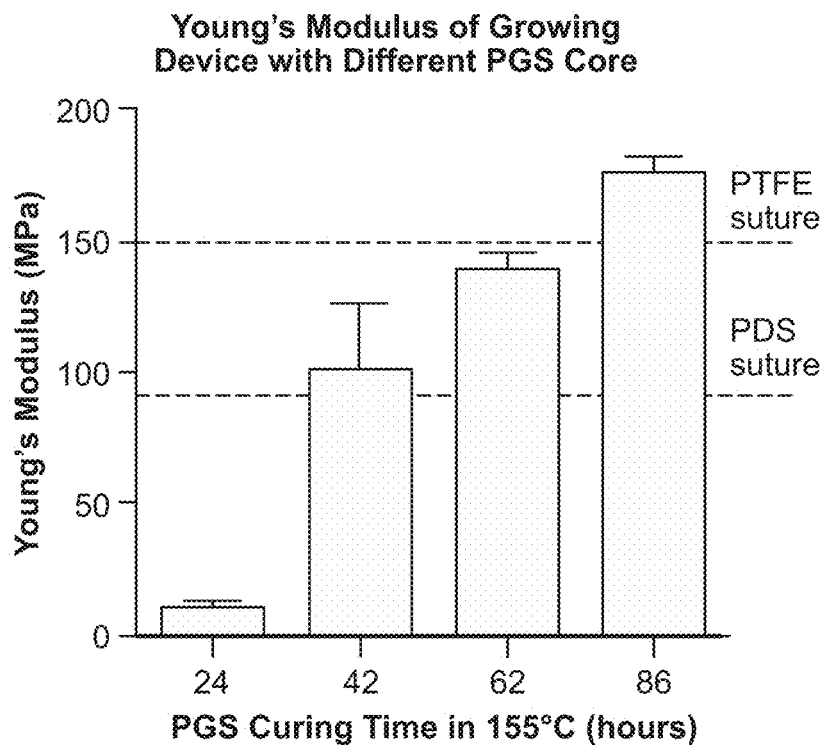
FIG. 8 depicts a graph showing varying Young's moduli resulting from different polymer curing times.

The inventors have also appreciated that different cure conditions result in different Young's moduli. FIG. 8 depicts a graph showing different Young's moduli resulting from different polymer curing times. FIG. 8 shows that using a longer cure time results in a higher Young's modulus. When the PGS pre-polymer was cured for 86 hours at 155° C., the Young's modulus for the resulting ESPGS reached 173 MPa. This greatly exceeded the compressive modulus of conventional PGS and also surpassed the Young's modulus of commercially available surgical sutures (e.g. PTFE and polydioxanone (PDS)).

In one embodiment, when the PGS pre-polymer was cured for 100 hours at 160° C., the Young's modulus for the resulting ESPGS was 200 MPa.

In some embodiments, the curing temperature and duration of the PGS pre-polymer when forming ESPGS can be varied based on clinical application to achieve a Young's Modulus of 100 to 200 MPa.

Mechanical testing was performed on an ADMET eXpert 7601 universal tester, equipped with a 50 N load cell and using the device with a cylindrical ESPGS core (length: 10 mm, diameter: 1.8 mm) and an outer UHMWPE braided sleeve. Uniaxial tensile testing was performed at a jog rate of 10 mm/min until sample failure (n>3 per condition), and Young's modulus was calculated as the slope at 20% strain. ESPGS cores cured for 24, 42, 62, or 86 hours were compared to evaluate the effect of polymer core mechanical strength on the overall tensile strength of the device.

The inventors have also appreciated that different cure conditions result in different crosslinking properties. In some embodiments, the crosslinking density of ESPGS ranges from 600 to 12,000 mol/m$^3$.

It should be appreciated that the inner core can be formed into different shapes, and that the shape of the inner core may impact degradation rate of the core.

In some cases, an increase in the core's surface-area-to-volume ratio will increase the degradation rate. In some embodiments, the inner core has a cylindrical shape. In other embodiments, the inner core may have a spherical shape, or may be a rectangular, square or triangular prism. In yet other embodiments, the inner core may be crescent-shaped, may be a curved arc or may be an irregular shape. In addition, the inner core may be a single piece, or may be a collection of a plurality of pieces. For example, the inner core may be a single rod-like piece. Alternatively, the inner core may be formed of a collection of small rods or cylinders.

Figure 9:
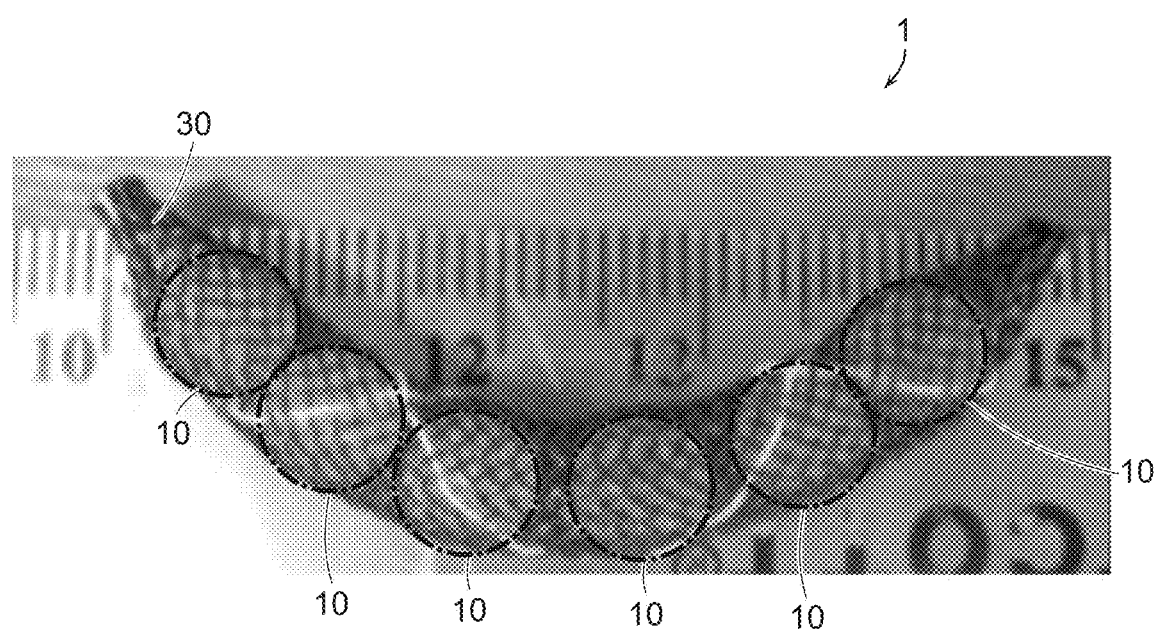
FIG. 9 depicts an embodiment of an implantable device in accordance with one aspect.

In one illustrative embodiment shown in FIG. 9, the inner core 10 is formed of a plurality of separate spheres that are held together by the outer element 30.

Alternatively, in other embodiments, the inner core is formed as a single piece of material that extends through the outer element.

It should be appreciated that the inner core may be made of materials other than polymer. For example, the inner core may be made of one or more metals that undergo erosion in vivo, or other material that undergoes erosion or other degradation in vivo. In some embodiments, the inner core need not be biodegradable. Instead, the material the inner core may become softer overtime. For example, in some embodiments, the inner core is made of a swellable material that takes up water or other liquid over time and become softer, such as polyacrylic acid.

The Outer Element

The outer element is configured to elongate in one or more dimensions in reaction to external forces. In some embodiments, the outer element is in the form of a braided element. In some embodiments, such as in the illustrative embodiments shown in FIGS. 1-5, the outer element is in the form of a biaxial braid. The growth profile of the device can be controlled in part using the geometry of the outer element. In the case of an outer element that is shaped as a tubular sleeve, the inventors have developed a mathematical model to describe the growth profile of the autonomously growing device as a function of the sleeve geometry. Sleeve parameters affecting the growth profile of the implantable device include: initial sleeve length ($L_i$), initial sleeve diameter ($D_i$), instantaneous sleeve diameter (D), and pitch (i.e. number of fiber turns, n, per unit length). With these inputs, instantaneous sleeve length (L) can be defined as a function of instantaneous sleeve diameter (D) as shown in the equation below:

$$L(D) = \sqrt{(\pi n D_i)^2 + L_i^2 - (\pi n D)^2} \qquad \text{Equation 1}$$

Instantaneous sleeve length is the length of the sleeve at a specific point in time, and instantaneous sleeve diameter is the diameter of the sleeve at that same specific point in time. Considering that the size of the inner core determines the instantaneous sleeve diameter, and that initial sleeve length is determined by the desired initial device size, the braid pitch is an important parameter of the sleeve for controlling the growth profile. Adjusting braid pitch allows for the creation of a range of unique braid elongation profiles.

Figure 10:
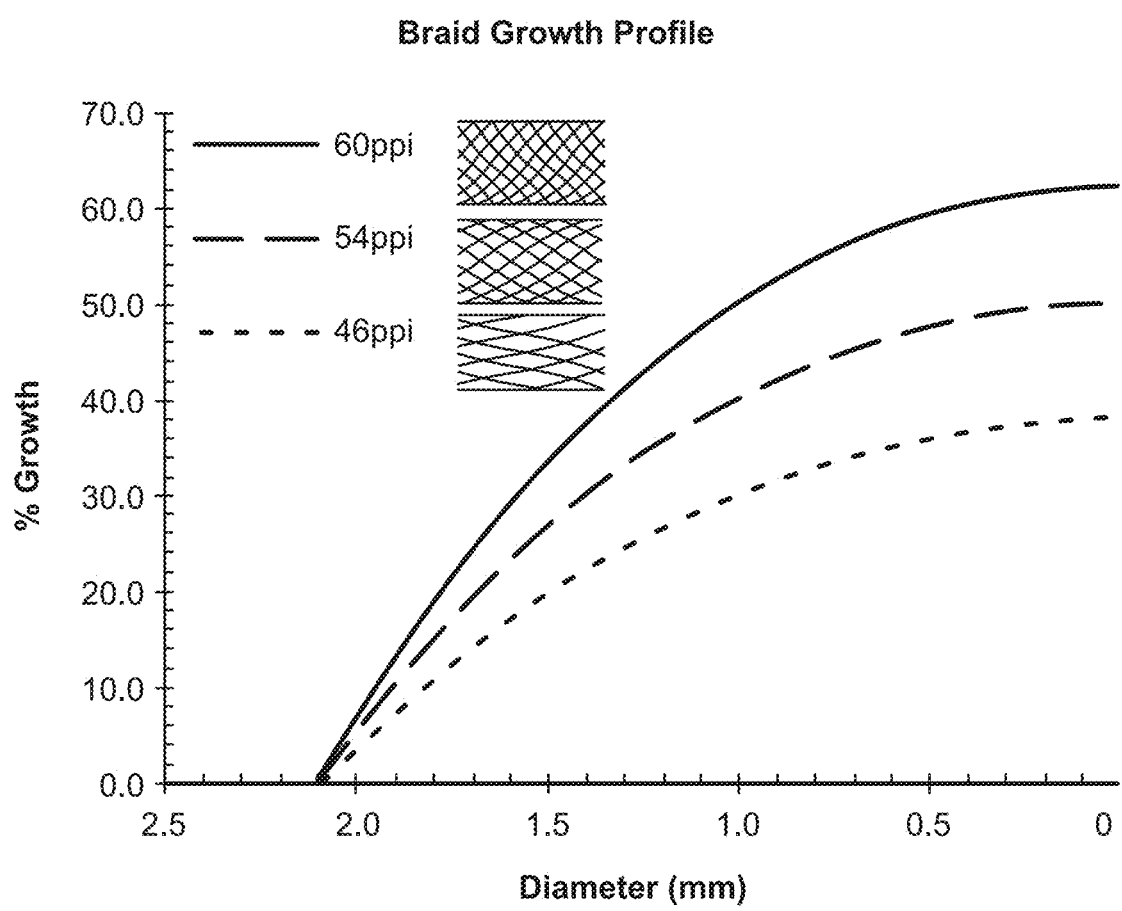
FIG. 10 depicts a graph showing the relationship between outer element length and outer element diameter at different braid pitches.

According to the mathematical model, devices with higher pitch demonstrate greater length change for a given diameter change of the outer element. FIG. 10 depicts the relationship between outer element length (expressed as percent growth) and outer element diameter at different braid pitches. The percent growth of the outer element length is inversely related to outer element diameter. Leaving other braid parameters constant, by increasing braid pitch (which can be defined by picks-per-inch (ppi)) from 46 ppi to 54 ppi to 60, a greater outer element elongation can be achieved. In one illustrative embodiment, an outer element with a 2 mm initial diameter ($D_i$) and pitches of 46, 54, and 60 ppi (picks-per-inch) can grow up to 38.4%, 50.6%, and 62.8%, respectively, when the inner core is fully degraded (FIG. 10). This indicates that the device's growth profile can be adjusted to fit different pediatric surgical applications or projected growth profiles.

The outer element can be configured to have different growth ranges. In some embodiments, the outer element can be configured to accommodate all of growth from infancy to adulthood such that the outer element can be implanted in infancy and grow with the patient into adulthood. In other embodiments, the device may be implanted in an older child, in which case the required amount of growth will likely be less. In some embodiments, the outer element may have a growth range of 10% to 180%, 100% to 180%, 150% to 180%, or 160% to 180%.

In some embodiments, an implantable device has a biaxially braided outer element having a pitch of 46 ppi (picks per inch), 54 ppi, or 60 ppi. In other embodiments, the outer element may have a pitch of 20 to 70 ppi. However, it should be understood that the outer element may employ other suitable pitches to adjust the growth profile of the implantable device.

In some embodiments, the initial device diameter ($D_i$) and initial device length ($L_i$) can be modified so that the braided outer element starts in a more shortened state. In this shortened state, the braided outer element's elongation capacity is increased (e.g., 180%) and can accommodate the aforementioned growth range.

Figure 11:
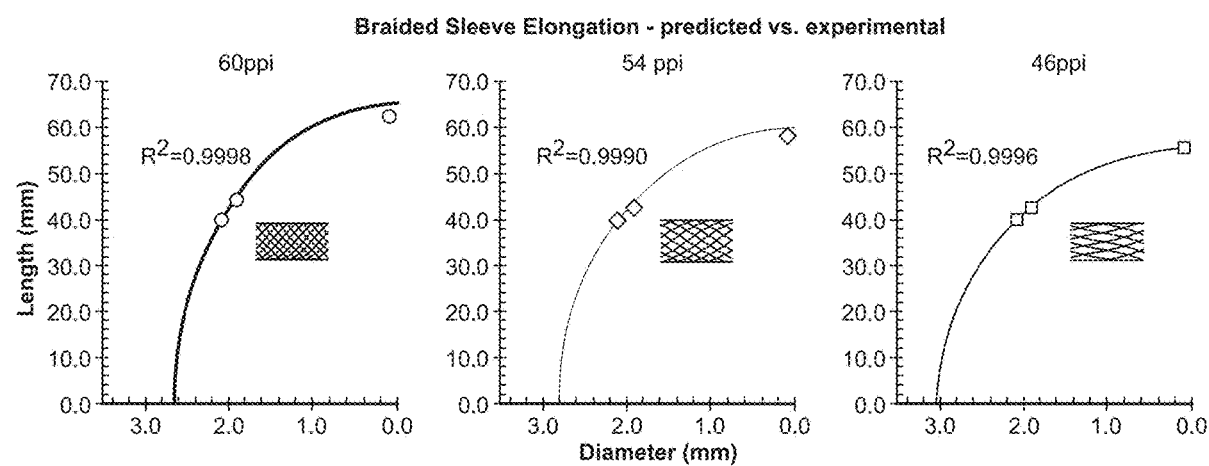
FIG. 11 depicts a graph comparing experimentally measured outer element lengths to values predicted from a mathematical model.

The device growth profile is not only tunable, it is predictable as well. As shown in FIG. 11, experimentally measured outer element lengths, represented by the dots, correlated well with the predicted values from the mathematical model, which is represented by the curves ($R^2 > 0.99$).

Figure 12:
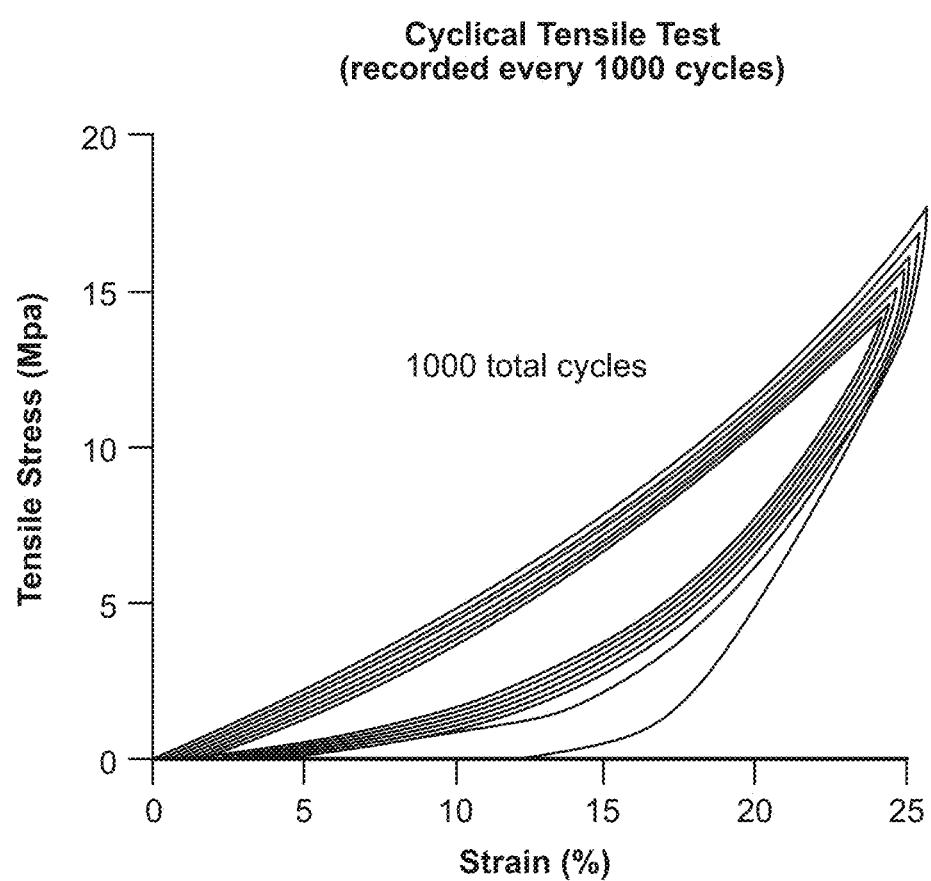
FIG. 12 depicts a graph showing the results of cyclic tensile testing on an implantable device in accordance with one aspect.

In addition, the implantable device holds up well against fatigue testing. The implantable device was subjected to cyclic tensile testing. As shown in FIG. 12, cyclic tensile testing demonstrates no evidence of device fatigue following 1000 cycles. Cyclical fatigue tensile testing (n=3) was performed at a jog rate of 50 mm/min, by sample extension until 30% elongation during 1000 consecutive cycles. Stress-strain curves were recorded every 100 cycles.

While the outer element may be a biaxial braid in some embodiments, it should be appreciated that other braid configurations are possible, such as a triaxial braid. In some embodiments, the strands of the braided outer element can themselves be braided, so that the braid strands elongate in addition to the overall outer element construct.

According to one aspect, the number and thickness of braid fibers could be reduced to create a "looser" braid that would allow greater access of water molecules to the polymer core and facilitate continued polymer degradation.

It should be appreciated that the outer element may be made of any suitable material. In some embodiments, the outer element is made of ultra-high-molecular-weight polyethylene (UHMWPE). Other materials such as polytetrafluoroethylene (PTFE), ethylene chlorotrifluoroethylene (ECTFE) and nitinol are also contemplated.

Assembly of the Device and Implantation

After the inner core is created and shaped, the inner core is inserted into the outer element. The outer element may be initially open on one or both ends to receive the inner core. After the inner core is inserted into the outer element, the one or more open ends of the outer element are closed by, for example, adhesive, suture or other string/thread/wrapping element used to tie the end(s) closed, mechanical fasteners, or any other suitable means. Alternatively, the outer element begins as a flat sheet that is wrapped around the inner core, and the outer element is then held closed by any suitable means such as those mentioned above.

In some embodiments, with the inner core disposed within the outer element, the outer element is initially pulled taut to tighten the outer element about the inner core.

Once assembled, the device is inserted into the implantation site and coupled to tissue located at the implantation site. The device may be coupled to tissue via suture, mechanical fasteners, adhesive, or any other suitable means. In some embodiments, sutures are looped through and/or tied to the outer element and then passed through tissue located at the implantation site to couple the outer element of the device to the tissue. As the tissue at the implantation site grows with the patient, the tissue exerts a force on the outer element of the device. Initially, the presence of the inner core within the outer element limits the outer element from elongating or otherwise growing with the tissue. As the inner core begins to degrade and/or soften over time, the outer element is permitted to elongate in the direction(s) of the force(s) exerted by the tissue. Such elongation may occur in one or more dimensions.

Example 1: Implantable Device Exhibiting Growth in One Dimension

In some embodiments, the device can be used to guide growth in one dimension, e.g. to treat abnormal long-bone growth. As an example of growth in one dimension, the growth of the device and its effect on bone growth were evaluated in a growing rat model. Young, growing male Wistar rats (150-200 g) underwent surgical implantation of the device along the left tibia, analogous to conventional implants used in children. Three animals received a growing device with a degradable ESPGS inner core, and three animals received a fixed-size device with a non-degradable PTFE inner core that would restrict growth, akin to existing surgical implants. The right tibia served as an internal control. All animals underwent interval micro computed-tomography (CT) imaging of each tibia to assess bone growth.

This study of growth in one dimension required a straight device to lie along the tibia. To create the inner core for the device, a PGS pre-polymer was cured within PTFE tubing for all 86 hours. Device manufacturing for the study involved insertion of the 1.8 mm diameter cylindrical ESPGS or PTFE inner core into the biaxially braided UHMWPE outer element. The UHMWPE braid had a pitch of 60 ppi, with a 1/1 intersecting pattern. Twenty-four fibers were used to construct the braided outer element, with each fiber being composed of twenty-five 12 nm filaments. Two animals received a PTFE (GOR-TEX) braided outer element for micro-CT imaging. Twelve CV-5 GOR-TEX sutures (W.L. Gore & Associates, Inc.), each 0.256 mm in diameter, were braided in a 1/1 intersecting pattern around a 2.1 mm mandrel. After inserting the inner core inside the braided outer element, a polypropylene (PROLENE) suture (Ethicon) was tied to each end of the device; these sutures were used to anchor the device to the bone during surgical implantation.

Figure 13A:
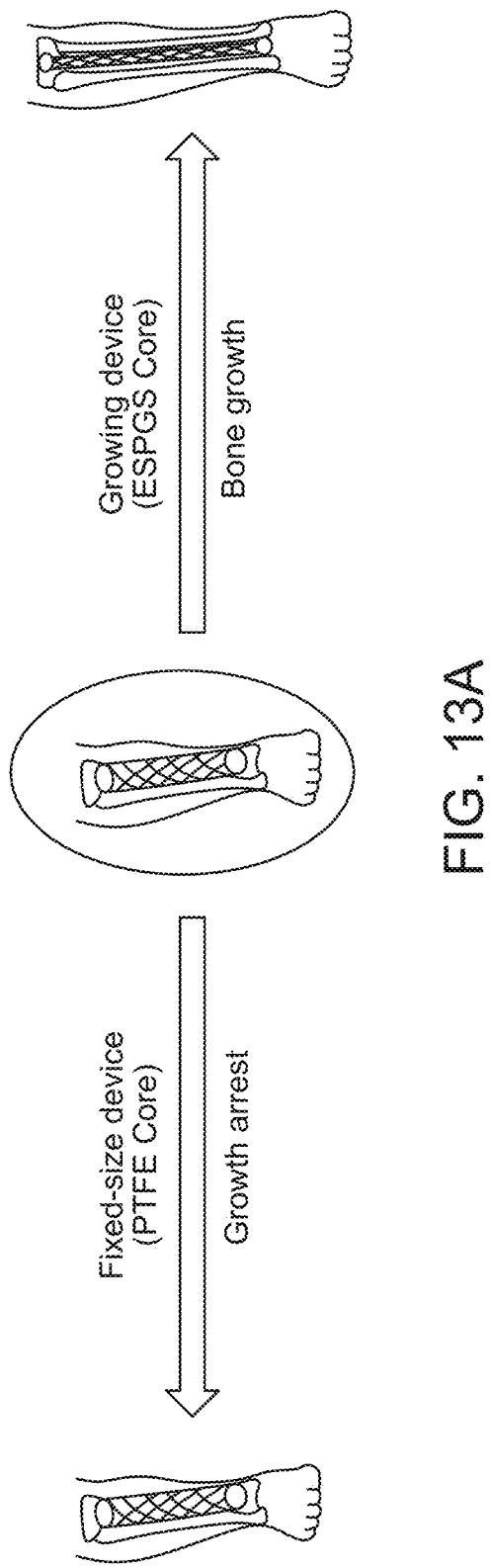
FIG. 13A is a cartoon depicting to types of device implants on a growing tibia.

FIGS. 13A-13E depict various diagrams, photographs and graphs associated with the study. FIG. 13A is a cartoon depicting two types of device implants on a growing tibia. The illustration to the right is a growing device with a degradable core that enables autonomous device growth and guided tibial growth. The illustration to the left is a fixed-size device with a nondegradable core that results in a fixed-size implant and restricted tibial growth.

Figure 13B:
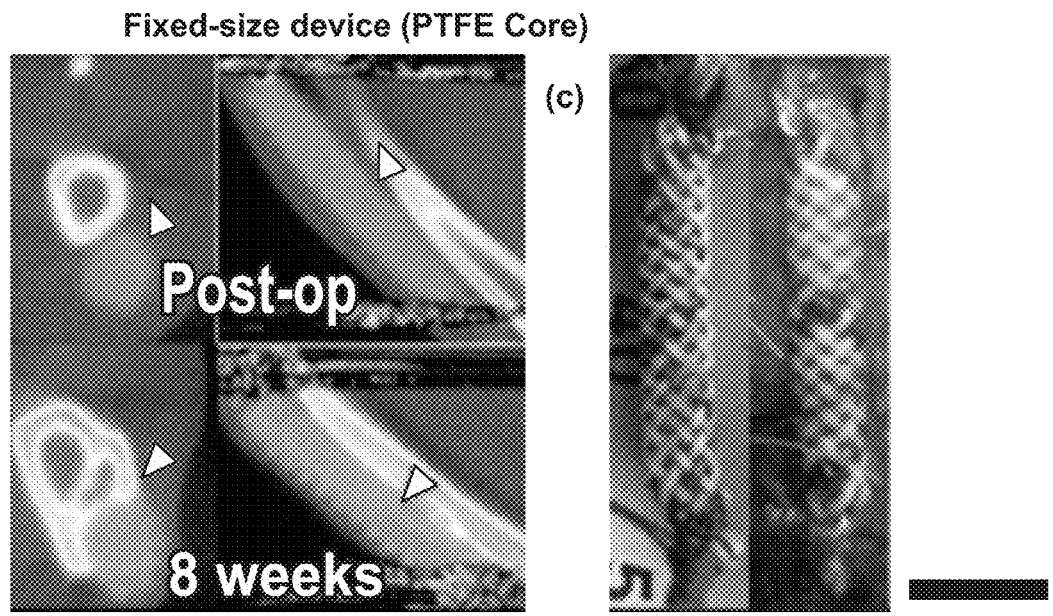
FIG. 13B shows micro-CT images in axial (left) and sagittal (right) cross-section of the fixed-size device at post-op and at 8 weeks after implantation.
Figure 13C:
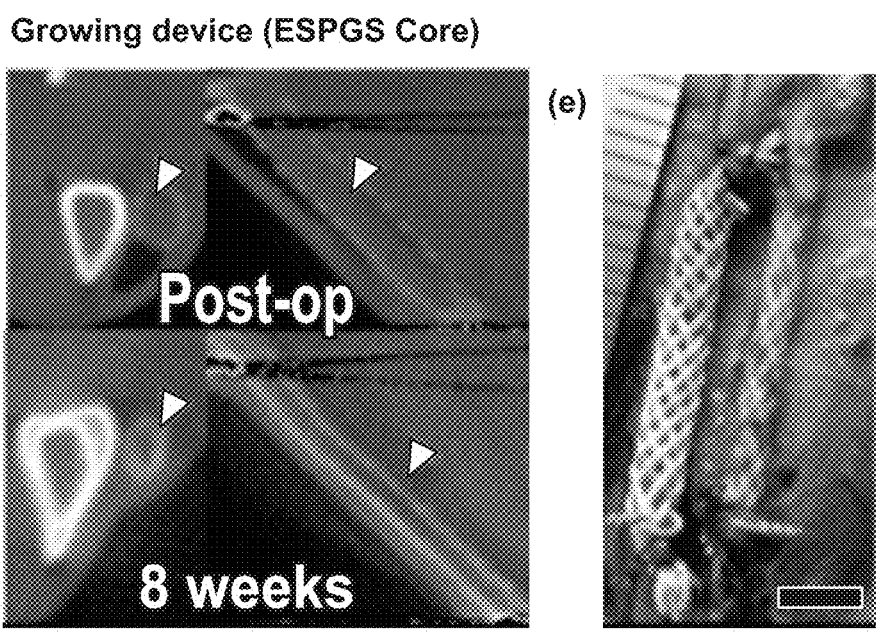
FIG. 13C is a side-by-side comparison of the fixed-size device at implant (left) and explant (right)

FIGS. 13B-13C depict images of the fixed-size device having a nondegradable PTFE core. FIG. 13B shows micro-CT images in axial (left) and sagittal (right) cross-section of the fixed-size device at post-op and at 8 weeks after implantation. The images indicate an absence of device growth over an 8-week survival. FIG. 13C is a side-by-side comparison of the fixed-size device at implant (left) and explant (right), which demonstrates no significant change in device length (scale bar=5 mm).

Figure 13D:
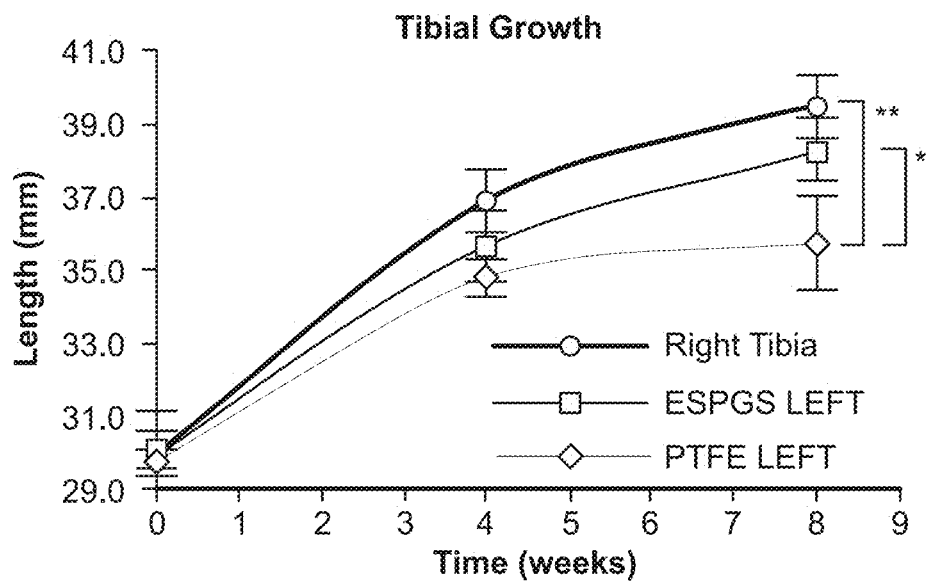
FIG. 13D shows micro-CT images in axial (left) and sagittal (right) cross-section of the growing device at post-op and at 8 weeks after implantation.
Figure 13E:
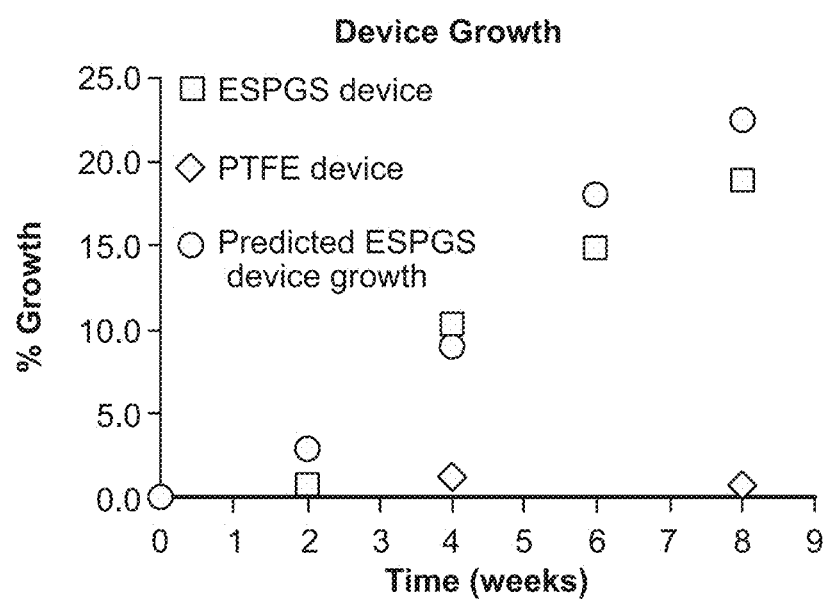
FIG. 13E is a side-by-side comparison of the growing device at implant (left) and explant (right)

FIGS. 13D-E are images of the growing device having a degradable ESPGS core. FIG. 13D shows micro-CT images in axial (left) and sagittal (right) cross-section of the growing device at post-op and at 8 weeks after implantation. The images indicate the thinning of ESPGS and concurrent lengthening of the device over an 8-week survival. FIG. 13E is a side-by-side comparison of the growing device at implant (left) and explant (right), which shows significant device elongation (scale bar=5 mm).

Implantation of the growing (ESPGS) versus fixed-size (PTFE) device led to distinct growth profiles (mean±s.d.). The fixed-size implant caused progressive growth restriction and ultimately growth arrest in the final 4 weeks. The growing implant provided mild growth restriction during first 4 weeks, but permitted physiologic bone growth in the last 4 weeks. By 8 weeks, the left tibial length with the fixed-size implant was statistically less than the left tibial length with the growing implant and the right tibial length. (* $P<0.05$,** $P<0.005$, one-way ANOVA post-hoc Tukey test).

For the growing device (ESPGS device), observed device growth was closely correlated with predicted growth. The growth profile of the fixed-size implant (PTFE device) is shown for comparison. (n=3 animals per group).

Device behavior translated to distinct tibial growth profiles for the two animal groups when compared to the contralateral (right) limb. PTFE animals experienced significant and progressive growth restriction. Overall growth was only 20.0% over 8 weeks compared with 32.0% growth in the unrestricted, right tibia (p=0.006). There was near arrest of left tibial growth in the final 4 weeks of survival: 2.6% left tibial growth in PTFE animals compared to 7.1% growth in the unrestricted, right tibia (p=0.01). By the end of the survival period, the left tibial length in the PTFE animals was significantly shorter than the right tibial length (p=0.004). The distinct growth trends in the final 4 weeks suggest that further growth differential would have occurred had the animals been survived longer. The latter 4 weeks of the study, in principle, represent a time when device removal/exchange would be necessary in a growing child to avoid excessive growth restriction.

The ESPGS animals, in contrast, experienced continued, guided bone growth that followed the physiologic, unrestricted right tibial growth pattern. When PTFE animals experienced significant growth restriction, left tibial growth in ESPGS animals was almost identical to right tibial growth (7.3% vs, 7.1%, p=0.27), and final tibial length was similar (38.3 mm vs. 39.5 mm, n.s.). Arrest of bone growth was avoided because of autonomous device elongation. In principle, this would prevent the need for device removal/exchange in a growing child.

Example 2: Implantable Device Exhibiting Growth in Two Dimensions

In some embodiments, the device can be used to guide growth in two dimensions, e.g. to treat heart defects. In one example, the device was used as an annuloplasty in a swine study. Curved ESPGS inner core pieces were created for the study. To create these curved pieces, straight polymer samples were removed from the PTFE tubing after 42 hours of curing. The polymer cylinders were then placed into an appropriate radius of curvature and cured at 155° C. for the remaining 44 hours. This division in curing intervals (42 and 44 hours) was chosen because sufficient curing within the straight PTFE tubing was required to produce well-formed polymer cylinders prior to inducing curvature.

Production of autonomously growing annuloplasty devices for the study involved insertion of a curved ESPGS inner core into a long segment of UHMWPE braided outer element. The braid/ESPGS composite was then attached to a mounting device for surgical implantation, utilizing polyglactin 910 (VICRYL) sutures (Ethicon).

Figure 14A:
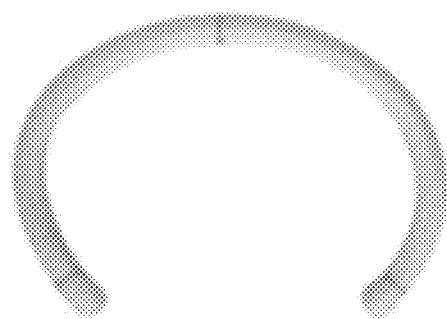
FIG. 14A is an image of a fixed-size annuloplasty device used in adults.
Figure 14B:
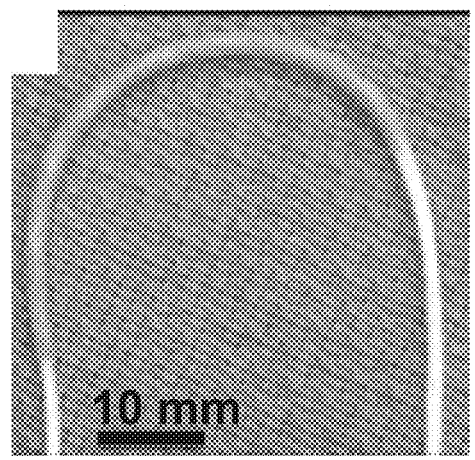
FIG. 14B is a photograph of a UHMWPE biaxially braided sleeve placed over a pre-curved cylindrical ESPGS polymer core.
Figure 14C:
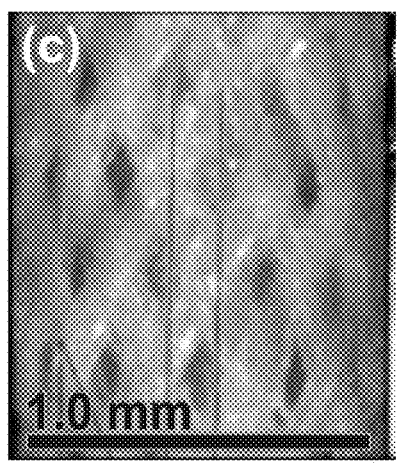
FIG. 14C is a photograph showing the braid pattern of the biaxially braided sleeve.
Figure 14D:
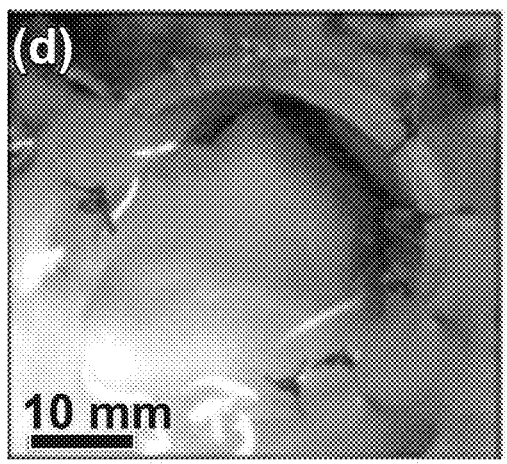
FIG. 14D is a photograph of an ex vivo demonstration of ring implantation with en face view of the tricuspid valve.
Figure 14E:
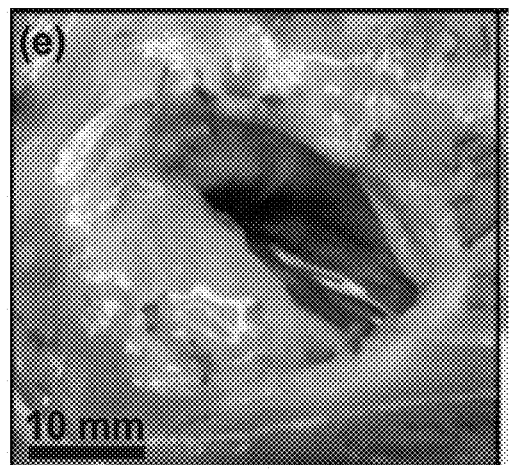
FIG. 14E is a photograph of an en face view of the freshly explanted tricuspid valve and ring 12 weeks after surgery.
Figure 14F:
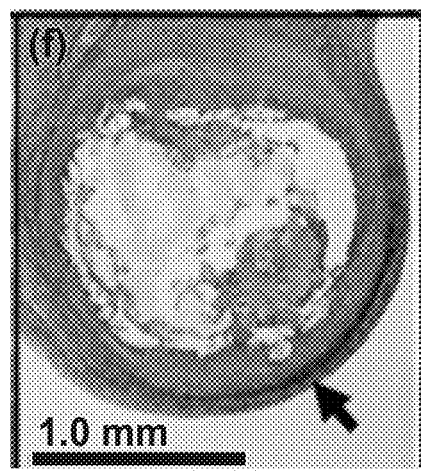
FIG. 14F depicts a cross-section through the explanted ring showing a collagen layer that grew over the growing device.
Figure 14G:
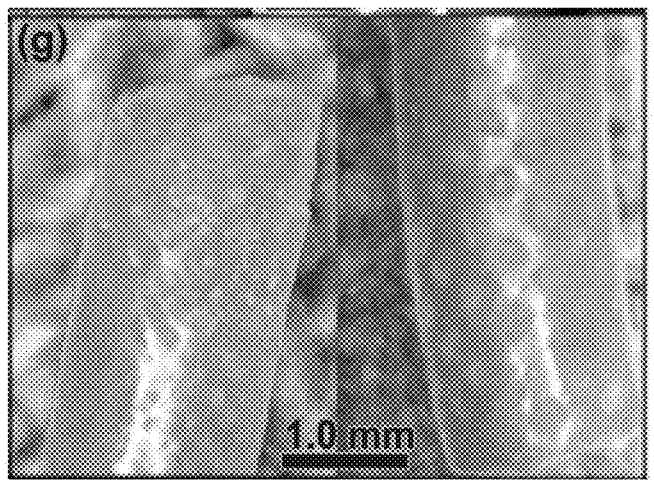
FIG. 14G depicts photographs of explanted ESPGS samples showing erosion at the surface of the polymer.
Figure 14H:
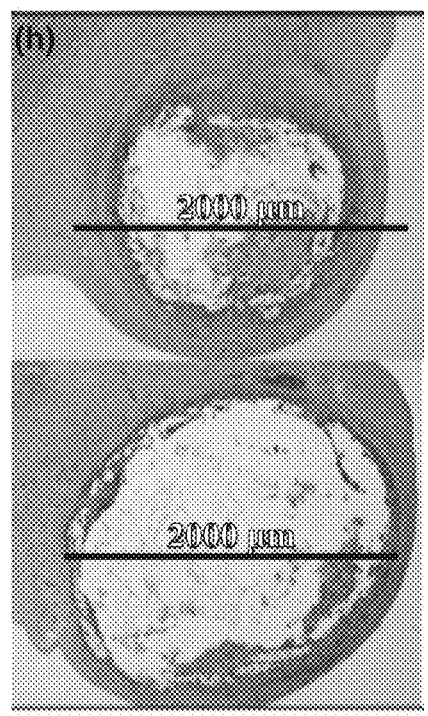
FIG. 14H depicts cross-sections through segments of the ring/annulus.

FIGS. 14B-14I depict various photographs and a graph associated with the study. FIG. 14B is a photograph of a UHMWPE biaxially braided sleeve placed over a pre-curved cylindrical ESPGS polymer core. FIG. 14C is a photograph showing the pattern of the biaxially braided sleeve. FIG. 14D is a photograph of an ex vivo demonstration of ring implantation with en face view of the tricuspid valve. In this example, the growing ring is secured to the valve annulus with a conventional suturing technique used for ring implantation in adults. The braided sleeve ends and body of the device are secured to annulus. FIG. 14E is a photograph of an en face view of the freshly explanted tricuspid valve and ring 12 weeks after surgery. The photographs show that the ring is intact and integrated into annular tissue without evidence of thrombus formation or dehiscence. FIG. 14F depicts a cross-section through the explanted ring showing a collagen layer (indicated by the arrow) that grew over the growing device. FIG. 14G depicts photographs of explanted ESPGS samples showing erosion at the surface of the polymer. FIG. 14H depicts cross-sections through segments of the ring/annulus. These cross-sections demonstrate regions of significant of core erosion with ring thinning (top) and areas of less significant core erosion with less ring thinning (bottom).

Figure 14I:
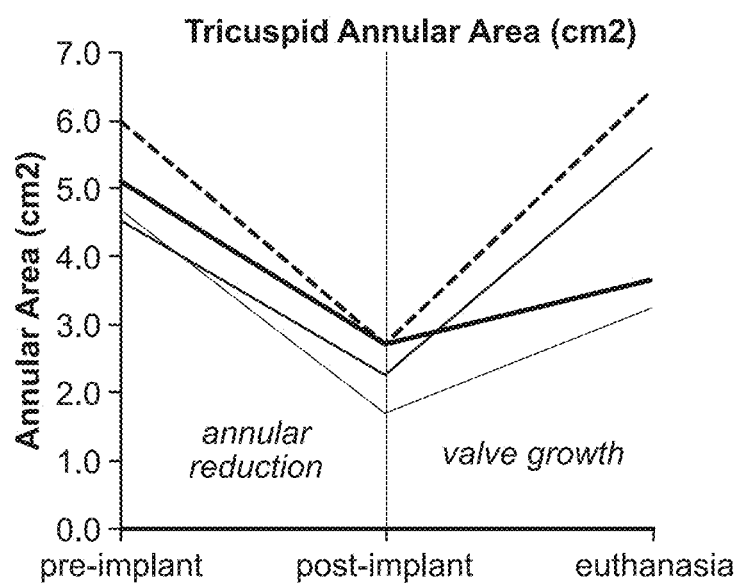
FIG. 14I depicts a graph of the annular area of the valve at three time points during the study: pre-implant, post-implant, and euthanasia.

FIG. 14I is a graph of the annular area of the valve at three time points during the study: pre-implant, post-implant, and euthanasia. All animals experienced valve reduction following ring implantation (left region), and experienced valve growth in the post-operative period (right region). Looking to the right-most end of the lines, the top line is the 12 week animal, the second line down is the 16 week animal, the third line down is the 5 week animal, and the bottom line is the 20 week animal.

In this study, four growing, female Yorkshire piglets (mean age 7.3±0.9 weeks) underwent surgical implantation of a growing annuloplasty ring on the tricuspid valve and were survived for 5, 12, 16, and 20 weeks to assess device behavior and valve growth. The growing annuloplasty device was shaped to have a similar geometry to commercially available, fixed-size annuloplasty rings, such as the fixed-size ring shown in FIG. 14A. The growing annuloplasty device, shown in FIG. 14B, was designed to reduce valve size at implantation akin to existing rings, and then expand to accommodate valve growth. The device included a UHMWPE braided sleeve over a curved cylindrical ESPGS core. A magnified view of the sleeve's biaxial braid configuration is shown in FIG. 14C. As shown in FIG. 14D, the ends of the braided sleeve were anchored to the valve annulus with sutures, and additional sutures were placed through the valve annulus and around the ring along its length. This enabled downsizing of the annulus and apposition of the ring to the annulus.

In all cases, the ring remained well-affixed to the valve annulus throughout the survival periods without evidence of dehiscence, as seen in FIG. 14E. This may have been promoted by the development of a collagen tissue layer over the device following implantation, as seen in FIG. 14F. ESPGS degradation was observed on direct inspection of explanted core segments, as seen in FIG. 14G. Cross-sections through explanted ring segments demonstrated areas of significant polymer core erosion following implantation, as seen in the top image of FIG. 14H, although there was regional variation with some segments experiencing less extensive core erosion, as seen in the bottom image of FIG. 14H.

Echocardiographic evaluation showed that the tricuspid valve in each animal was effectively downsized by the growing ring prototype at the time of surgery (see FIG. 14I, pre-implant to post-implant). This demonstrated that the growing ring could withstand intra-cardiac forces and effectively constrain the valve, as is necessary in heart valve repair surgeries. Valve reduction was then followed by some degree of valve growth after device implantation (see FIG. 14I, post-implant to euthanasia).

As discussed above, in all animals, the ring remained firmly affixed to the valve annulus throughout the survival period. ESPGS erosion occurred early in the survival period, as evidenced by the decrease in ESPGS diameter over the first five weeks. Normal valve growth, which followed BSA growth, was achieved during the first several weeks after ring implantation, concurrent with when ESPGS was degrading. Beyond 5 weeks, there was minimal change in ESPGS diameter. The resultant fixed size of the implant at later survival periods correlated with a slowing of valve growth relative to BSA growth. This association between polymer degradation and valve growth lends support to the fundamental mechanistic phenomenon observed in the rat model: inner ESPGS degradation enabled device growth, and tissue growth was accommodated. Conversely, in circumstances of fixed inner polymer size (i.e. a nondegradable PTFE inner core in the rat model control group, or slowing of ESPGS degradation in the swine model), the implant did not grow, and tissue growth was restricted.

This study demonstrated the ability of the growing annuloplasty device to control heart valve growth.

It should be understood that the foregoing description is intended merely to be illustrative thereof and that other embodiments, modifications, and equivalents are within the scope of the present disclosure recited in the claims appended hereto. Further, although each embodiment described above includes certain features, the present disclosure is not limited in this respect. Thus, one or more of the above-described or other features of the implantable device or methods of use, may be employed singularly or in any suitable combination, as the present disclosure and the claims are not limited to a specific embodiment.

The invention claimed is:

1. A method of forming a biodegradable polymer, comprising:
   polycondensation of an equimolar ratio of glycerol and sebacic acid at 120 degrees Celsius (°C) for 8 hours under dry nitrogen and for 16 hours in vacuum to form a pre-polymer; and
   curing the pre-polymer in a vacuum at a temperature of 140° C. to 160° C. for 40 to 100 hours.

2. The method of claim 1, further comprising:
   putting the pre-polymer in a mold.

3. The method of claim 2, wherein the mold is curved.

4. A polymer comprising:
   a Young's Modulus of greater than 5 megapascals (MPa); and
   a crosslinking density of 600 to 12,000 moles per cubic meter,
   wherein the polymer is formed from curing a poly(glycerol sebacate) pre-polymer in vacuum at a temperature of 140° C. to 160° C. for 40 to 100 hours.

* * * * *

UNITED STATES PATENT AND TRADEMARK OFFICE
CERTIFICATE OF CORRECTION

| | |
|---|---|
| PATENT NO. | : 11,433,161 B2 |
| APPLICATION NO. | : 17/146464 |
| DATED | : September 6, 2022 |
| INVENTOR(S) | : Eric N. Feins et al. |

It is certified that error appears in the above-identified patent and that said Letters Patent is hereby corrected as shown below:

In the Specification

At Column 1, Line 18, below the RELATED APPLICATIONS paragraph, please add the following new paragraph:
FEDERALLY SPONSORED RESEARCH
This invention was made with government support under Grant Number HL073647, awarded by the National Institutes of Health. The Government has certain rights in the invention.

Signed and Sealed this
Twenty-first Day of February, 2023

Katherine Kelly Vidal
*Director of the United States Patent and Trademark Office*